United States Patent [19]

Becht

[11] Patent Number: 4,480,640
[45] Date of Patent: Nov. 6, 1984

[54] LIGATING DEVICE

[75] Inventor: Carl T. Becht, Cincinnati, Ohio

[73] Assignee: Senco Products, Inc., Cincinnati, Ohio

[21] Appl. No.: 142,676

[22] Filed: Apr. 22, 1980

[51] Int. Cl.³ .......................................... A61B 17/12
[52] U.S. Cl. .................................... 128/325; 72/410; 29/243.56; 227/DIG. 1
[58] Field of Search ............ 128/325, 334 R; 72/410; 29/243.56; 227/DIG. 1, DIG. 1 B, DIG. 1 C

[56] References Cited

U.S. PATENT DOCUMENTS

| 2,733,441 | 2/1956 | White | 227/DIG. 1 B X |
| 2,968,041 | 1/1961 | Skold | 227/DIG. 1 B X |
| 3,234,636 | 2/1966 | Brown | 227/DIG. 1 B X |
| 3,844,289 | 10/1974 | Noiles | 227/DIG. 1 B X |
| 4,226,242 | 10/1980 | Jarvik | 128/325 |

FOREIGN PATENT DOCUMENTS 875  7/1979  European Pat. Off. ............ 128/325

Primary Examiner—Michael H. Thaler
Attorney, Agent, or Firm—Frost & Jacobs

[57] ABSTRACT

There is disclosed a ligating device which includes a magazine housing containing a supply of ligating clips. The device has two handles and when these handles are squeezed together they clamp a ligating clip about a vessel to be ligated. When the handles are released, a linkage between one of the handles and the magazine, feeds a succeeding ligating clip into position for use. Thus, the feed of clips in the device is entirely independent of any effort on the part of the surgeon using the device.

10 Claims, 10 Drawing Figures

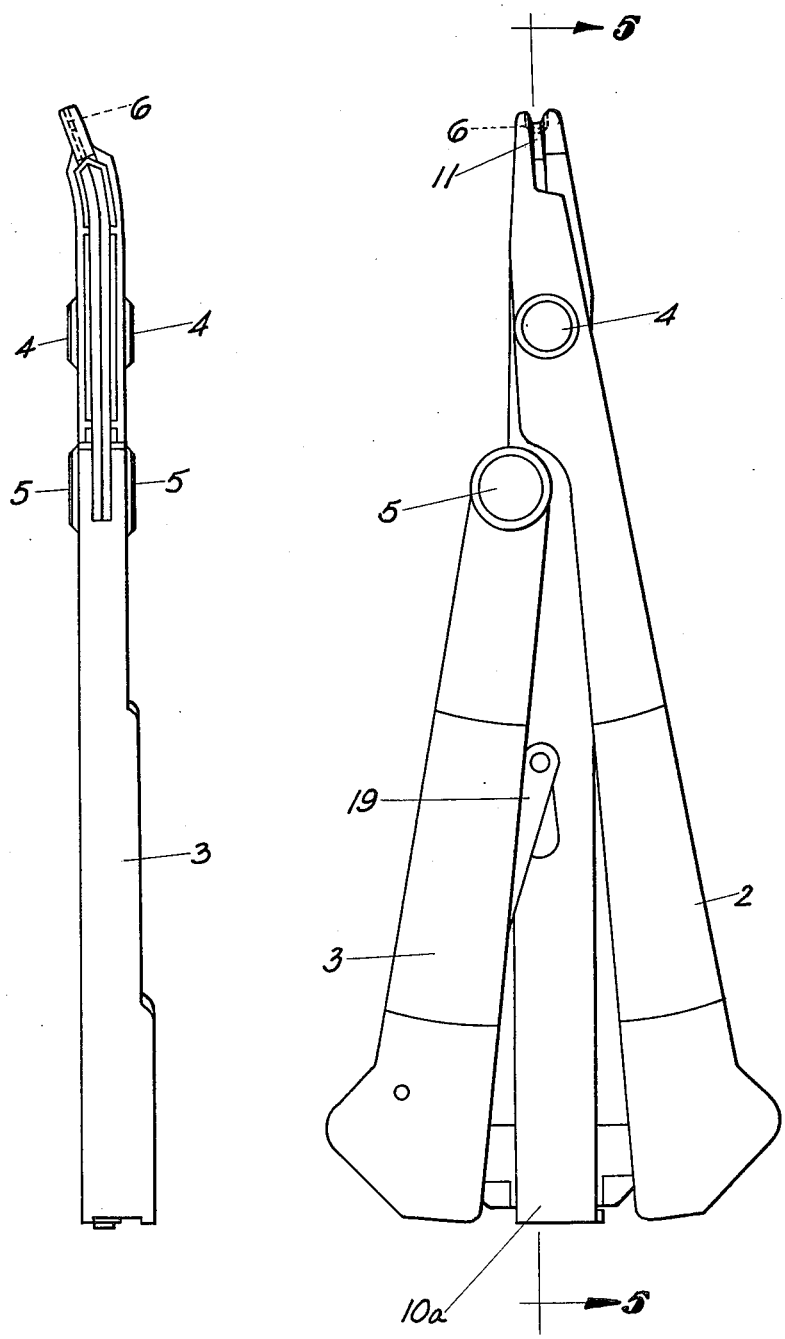

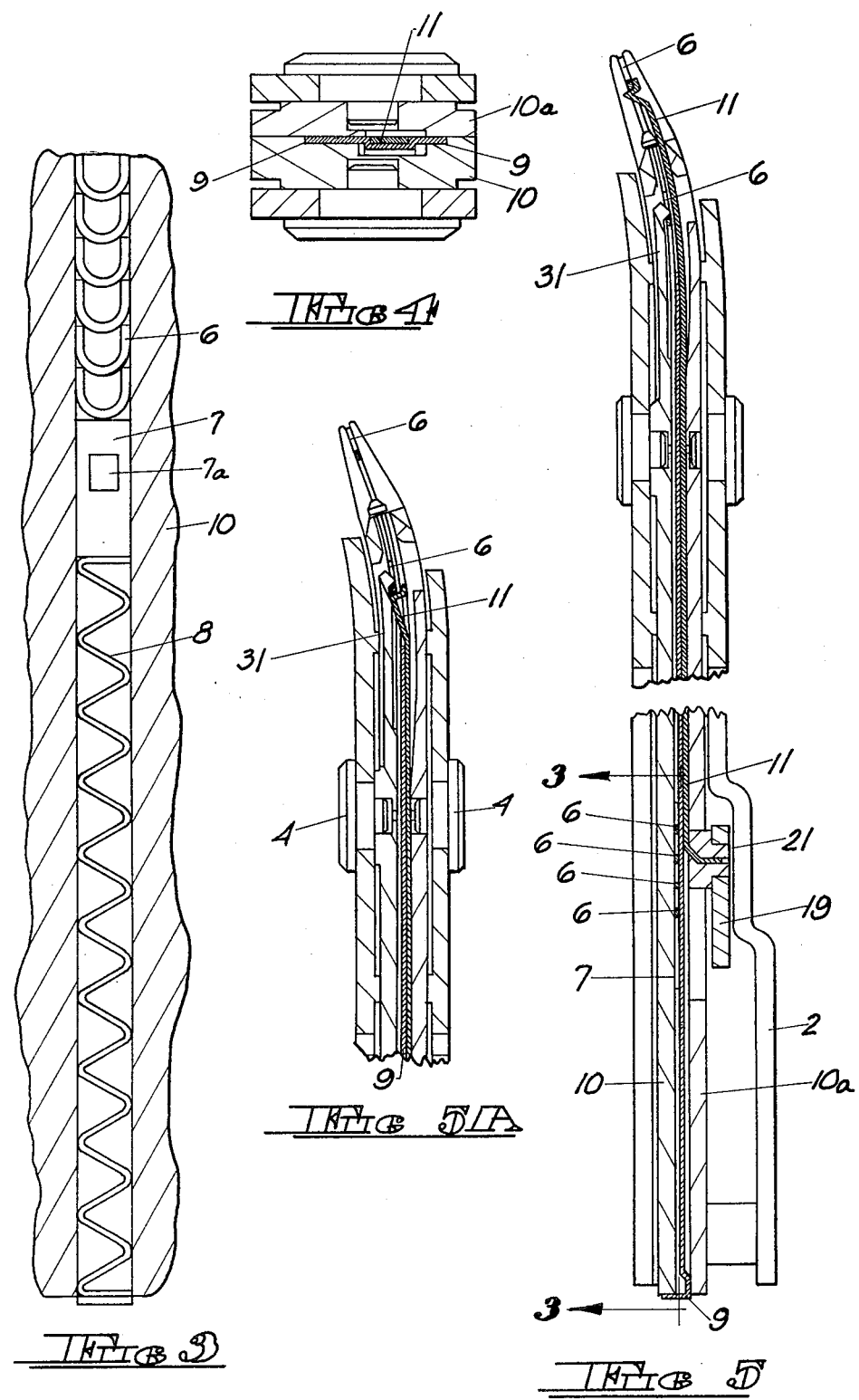

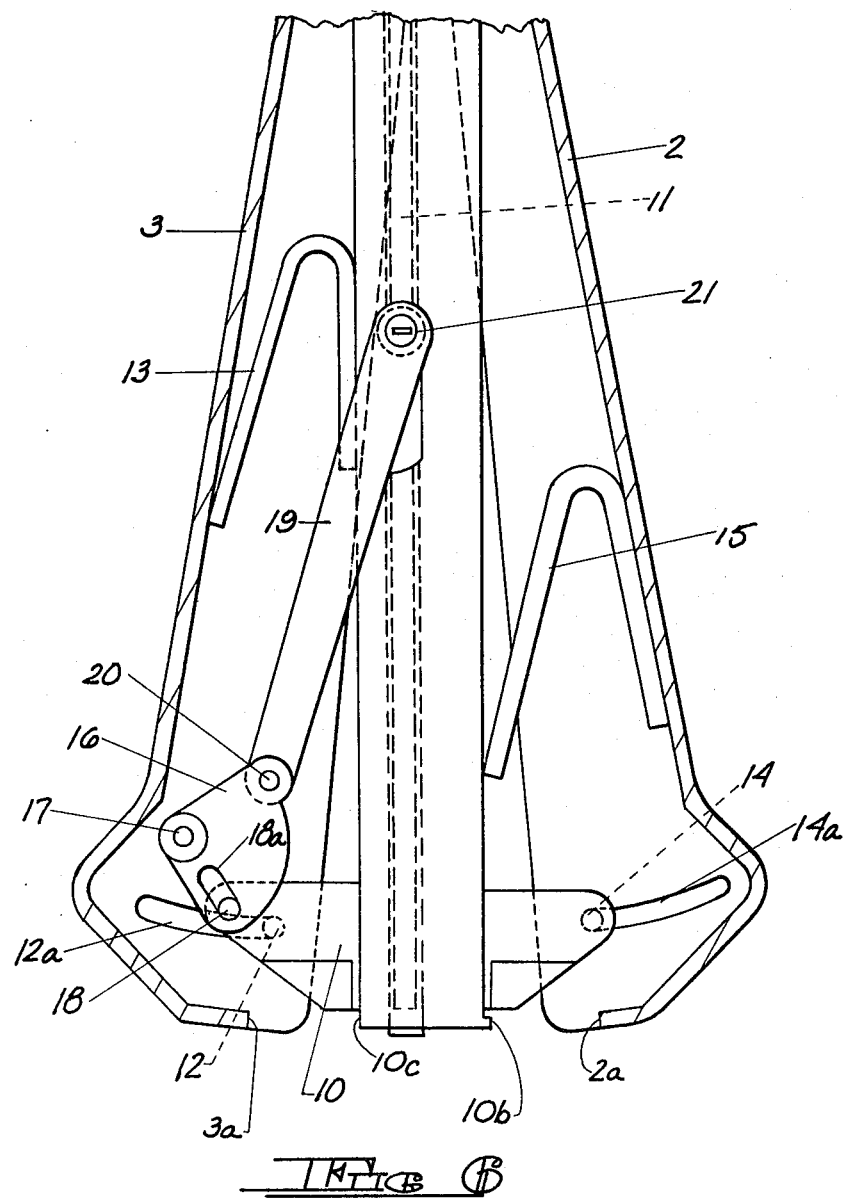

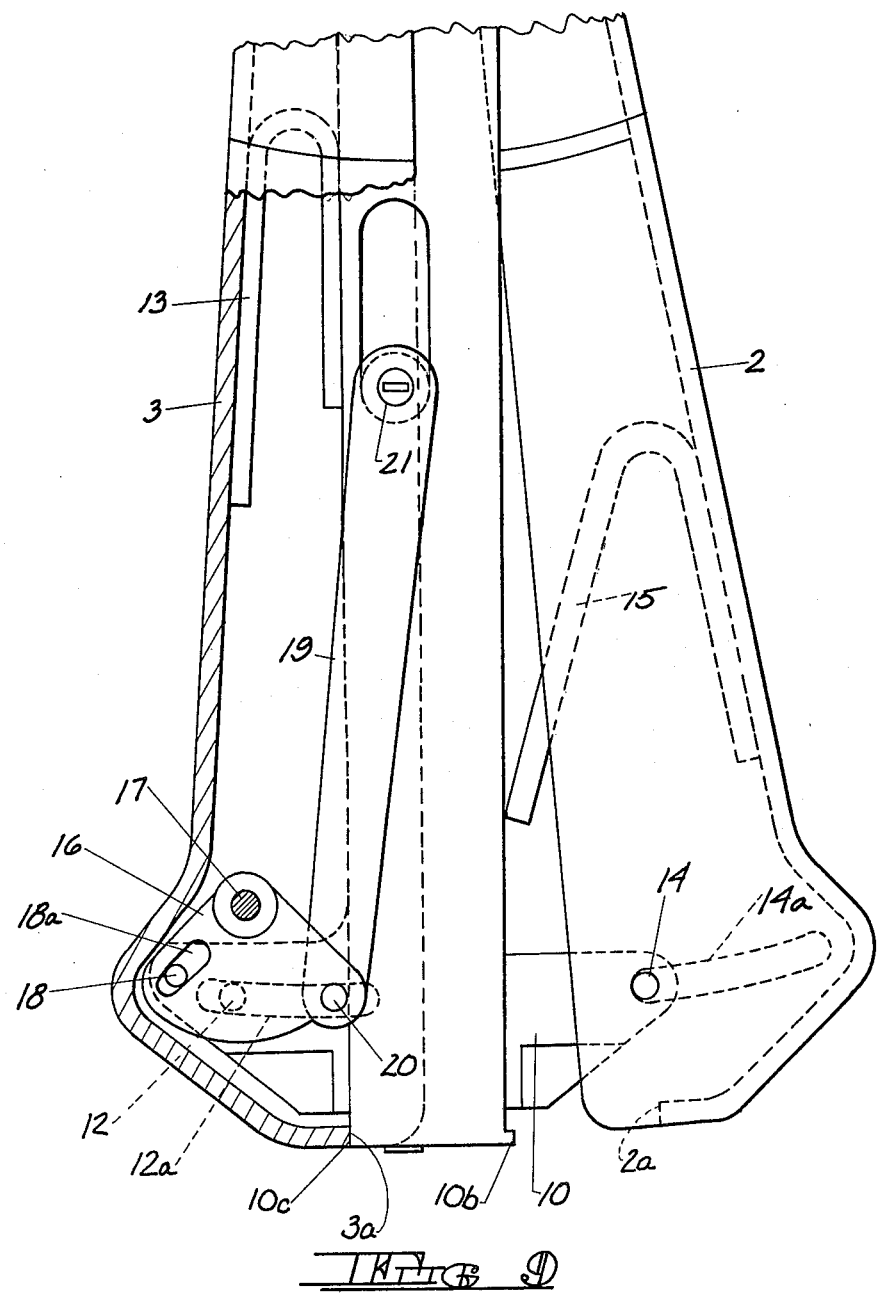

LIGATING DEVICE

TECHNICAL FIELD

This application is related to copending application Ser. No. 6/142,675 filed Apr. 22, 1980.

BACKGROUND OF THE INVENTION

Ligating devices are well known and are used in surgical operations wherever it is necessary to clamp off permanently a vessel, such as a vein. Generally, a U-shaped clip is placed about the vessel to be ligated and then the ligator is actuated to clamp the vessel, by means of the clip. In all heretofore available ligators, the actuation of the ligating mechanism also functioned to feed a clip into position to be formed. Thus, the effort of the surgeon not only did the clamping of the clip, but also the feeding of the clips into position to be clamped.

In the copending Becht application referred to above, a spring urged magazine for clips was provided in one of the two handle members of the ligator and as soon as one clip was clamped, a spring fed a succeeding ligator in position for the next clamping operaton. Other known ligating devices are disclosed in the U.S. Pat. No. 4,152,920 and in U.S. Pat. No. 4,166,466 dated Sept. 4, 1979, in the name of R. J. Jarvick.

BRIEF DESCRIPTION OF THE INVENTION

According to the present invention, a magazine housing is provided and two handles for operating the ligator are pivotally secured to the magazine housing. In the magazine housing, a supply of clips is provided and a feeding plate is disposed in the housing behind the clips and is urged toward the distal end of the device by means of a spring. The foremost clip in the magazine is fed by means of a feed finger into the forming portion of the device, at the distal end thereof. Succeeding clips are urged by the above mentioned spring against a magazine housing detent.

Linkage is provided between the magazine feeding finger and one of the handles of the device, such that when the device is actuated by squeezing the handles together, the feeding finger is retracted from behind the leading clip, which is in position to be formed, and thereafter, by further actuation of the handles, the leading clip is formed about the vessel to be ligated. As the handles are released, the feeding finger is moved forward, toward the distal end of the device and pushes the leading clip remaining in the magazine past the magazine housing detent, in position to be formed. Thus, in this device also, the surgeon's effort in operating the device is in no way involved in the feed of clips, but only in the forming of the clips about the vessel to be ligated.

BRIEF DESCRIPTION OF THE FIGURES OF THE DRAWING

FIG. 1 is a plan view of the device, according to the invention.

FIG. 2 is a side elevational view thereof.

FIG. 3 is a partial, cross sectional view, taken along the line 3—3 of FIG. 5.

FIG. 4 is a cross sectional view, taken along the line 4—4 of FIG. 7.

FIG. 5 is a cross sectional view, taken along the line 5—5 of FIG. 1.

FIG. 5a is a fragmentary view, similar to FIG. 5 showing the feed finger in its retracted position.

FIG. 6 is a fragmentary, cross sectional view, through the proximal end of the device, showing the ends of the handles in their normal position.

FIG. 9 is a fragmentary view, similar to FIG. 6, but showing the handles of the device partially actuated.

DETAILED DESCRIPTION

Figure 7:
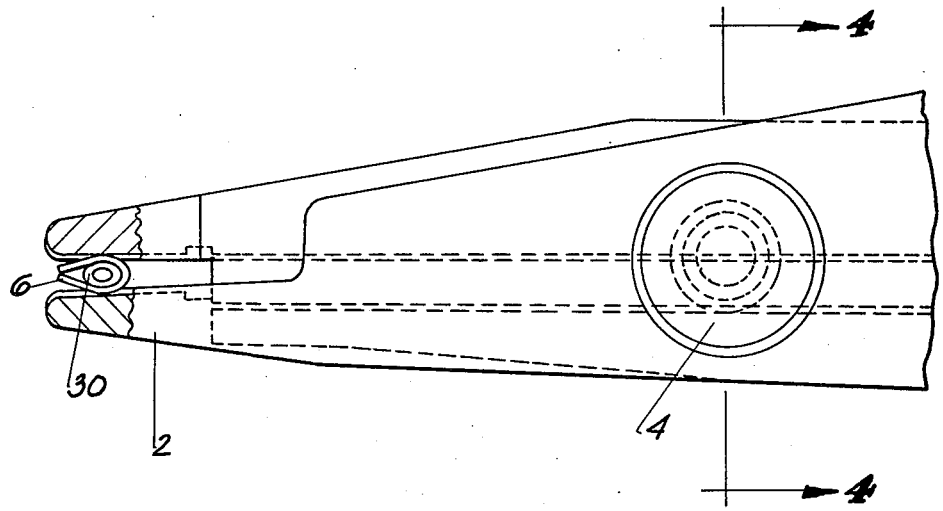
FIG. 7 is a partial, plan view of the distal end of the device, with a ligating clip partially closed.

As best seen in FIG. 1, the ligating device comprises a magazine housing 10 having a cover 10a and a pair of handles 2 and 3. The handle 2 is pivotally secured to the magazine housing 10, by means of pivot pins 4, while the handle 3 is pivotally secured to the magazine housing by the pivot pins 5. It should be noted, that the handle 2 is the clip forming handle, while the handle 3 is the clip feeding handle.

As best seen in FIG. 3, the magazine housing 10, includes a supply of clips 6 disposed in end-to-end relation, a feeder plate 7 and a spring 8.

As best seen in FIG. 4, the magazine housing 10, is provided with a cover 10a. The feed finger track plate is indicated at 9 and it houses the feed finger 11. Thus, the feed finger 11, is guided in the feed finger track plate 9. The parts are held in position in the magazine by means of the magazine housing cover 10a, which is attached to the magazine housing 10, in any suitable manner.

As is best seen in FIG. 6, the clip feeding handle 3, is biased normally against a stop pin 12, by means of the resilient element 13. The clip forming handle 2, is normally biased against the stop pin 14, by the resilient member 15. A bell crank 16, is pivotally mounted in the handle 3, by pivot pin 17. The bell crank 16, is operatively connected to the actuating pin 8, which is fixedly mounted in the magazine housing 10. The bell crank 16, is also operatively connected to an actuation rod 19, by a pivot pin 20 and the other end of the actuation rod 19, houses a bushing 21, which is operatively connected to the feed finger 11. It must be observed that the resilient member 15, which biases the clip forming handle 2, against the stop pin 14 (which moves in the arcuate slot 14a) is stronger than the resilient member 13 which biases the handle 3 against the stop pin 12 (which moves in the arcuate slot 12a). The pin 18 can move in the slot 18a.

In the Figures, the vessel to be ligated is indicated at 30. Referring to FIGS. 5 and 5a there is shown a magazine housing detent 31 and it will be clear that the spring 8 and the feeder plate 7, bear against the last of the supply of clips 6 and urge them toward the distal end of the device and up against the magazine housing detent 31.

OPERATION OF THE LIGATOR

From the foregoing description, it should now be clear that, assuming a supply of clips to be disposed in the magazing housing 10-10a, the spring 8 and the feeder plate 7, will urge the supply of clips 6 forwardly, toward the distal end of the device and up against the magazine housing detent 31. The first operation of the device, will have to involve a squeezing of the handles together, without attempting to place a clip, simply so that the feeding finger will be retracted from the distal end of the device and by contact with the detent 31, will be caused to hop over the detent 31 and move to a position behind the next clip in the magazine. Then as the handles are released, the feed finger 11, will move from the position shown in FIG. 5a, to the position shown in FIG. 5, where it has moved the first clip in the magazine into the forming portion of the device, ready for emplacement to ligate a vessel. As feed finger 11 is pushed forward against the first clip in the magazine, the detent 31 is depressed, permitting the feed finger 11 and the first clip 6 to advance to the forming portion of the device. When the feed finger 11 and the first clip 6 have passed over the depressed detent 31, it is permitted to spring back into place, thereby positioning the next clip to be fed.

The way in which this is accomplished, can best been seen by a comparison of FIGS. 6 and 9. FIG. 6 shows the proximal end of the device, in its unactuated position. It will be seen that the resilient member 15, urges the forming handle 2 in a counterclockwise direction, so that the handle stops in a position with the stop pin 14, against the left hand end of the slot 14a, as seen in FIGS. 6 and 9. At the same time, the feeding handle 3 is forced by its resilient member 13, to a position in a clockwise direction, such that the stop pin 12 abuts the right hand end of the slot 12a.

Upon initial actuation of the device, since the resilient member 13 is weaker than the member 15, the handle member 3 will start to move in a counterclockwise direction, and as it does so, the pin 18 acting in the slot 18a, causes the bell crank 16 to move in a clockwise direction and to pull the actuating link 19 downward, as seen in FIGS. 6 and 9. This is what causes the feeding finger to be retracted to a position to feed the next clip.

Figure 8:
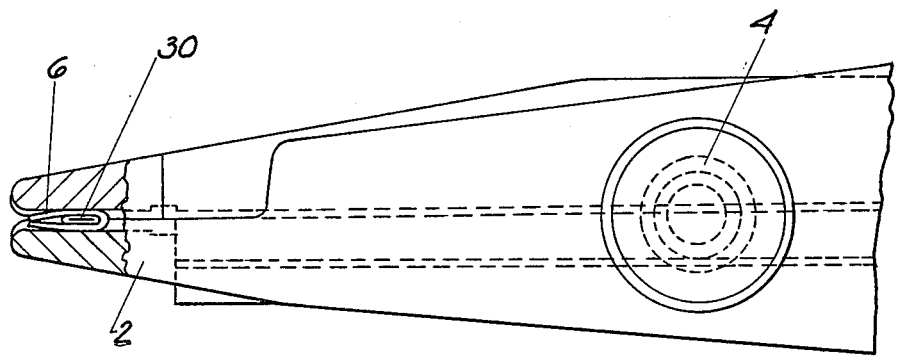
FIG. 8 is a view similar to FIG. 7, showing the ligating clip fully closed.

When the handle member 3 has moved to a position where surface 3a of handle member 3 is in contact with surface 10a of magazine 10, the resilient element 15 begins to yield and the clamping handle member 2 then begins to close the clip 6, as shown in FIG. 7. It will be noted, that the clamp closes with its open end first, so as to capture the vessel 30. Further compression of the clip then completely ligates it as seen in FIG. 8. Surface 2a of forming handle 2, in cooperation with surface 10b of magazine 10 serves as a stop for clip formation, thereby prohibiting overload of the device.

As the surgeon releases the handle members 2 and 3, the linkage described in connection with FIGS. 6 and 9 operates in the reverse direction and causes the feed finger, which is now in the position shown in FIG. 5a, to move toward the distal end of the device to the position, shown in FIG. 5, advancing the next clip 6 into position to be clamped about a vessel.

It will be seen that the feeding of clips, into position for clamping, is independent of any effort on the part of the surgeon. It is accomplished when the surgeon releases the handles 2 and 3.

By reference to FIG. 3, it will be noted that there is a hole 7a in the plate 7. The purpose of this is to prevent utilization of the ligator when all the ligating clips have been expended. It accomplishes this by the feed finger cooperating with the hole 7a, to advance the feeder plate 7 into the forming area of the device.

It will be noted that once the handles have been actuated in a new ligator there will be a clip in position to be formed, when the ligator is in its unactuated position. Thereafter, each time a clip is emplaced and the handles are released, another clip is fed into position for subsequent emplacement. In actual practice, when a ligator is manufactured, it is tested several times before packaging and sterilization. Thus when a ligator is unpacked for use in the operating room, it will already have a clip in position to be formed.

It will be clear that numerous modifications may be made without departing from the spirit of the invention and therefore no limitation which is not expressly set forth in the claims, is intended and no such limitation should be implied.

What is claimed is:

1. A surgical ligator to locate and clamp a substantially inverted U-shaped clip about a tubular member to close off the tubular member, said ligator comprising a magazine housing containing a supply of said clips, said housing at its distal end terminating in a clip forming portion, said ligator having a clip forming handle and a clip feeding handle to be grasped by the hand of a surgeon in pliers-like fashion, said clip forming handle being pivotally secured to said magazine housing and having a clip forming end configured to cooperate with said clip forming portion of said magazine housing to clamp a clip about a tubular member, said clip forming handle being shiftable by the hand of a surgeon between an open unactuated position and an actuated closed clip-clamping position, said clip feeding handle being pivotally secured to said magazine housing, said clip feeding handle being shiftable by the same hand of a surgeon between an open unactuated position and a close actuated position, means operatively connected to said clip feeding handle to shift the forwardmost clip of said supply from said magazine housing to a position between said clip forming portion of said magazine housing and said clip forming end of said clip forming handle upon the shifting of said clip feeding handle from said actuated position to said unactuated position, and means to insure proper sequential movement of said handles.

2. The structure claimed in claim 1 having a magazine housing detent means adjacent said forming portion, and means continuously urging said supply of clips against said detent means, said means operative upon release of said clip feeding handle serving to push a leading clip past said detent means between said forming portion of said magazine housing and said clip forming end of said clip forming handle.

3. The structure claimed in claim 2 wherein a feeder plate is disposed in said magazine housing behind said supply of clips, and a spring is arranged behind said feeder plate to urge said supply of clips continuously toward said forming portion and against said detent, said means to shift said forwardmost clip comprising a feeding finger in said magazine housing and a linkage between said feeding finger and said clip feeding handle, such that said feeding finger is retracted from said forming portion when said clip feeding handle is shifted from said open unactuated postion to said closed actuated position, and advanced toward said forming portion when said clip feeding handle is released to said open unactuated position, to push a clip past said detent and between said forming portion of said magazine housing and said forming end of said clip forming handle to be clamped on the next actuation of said handles.

4. The structure of claim 3 wherein said forming handle is pivotally secured to said magazine housing adjacent said forming portion for mechanical advantage, and said feeding handle is pivotally secured to said magazine housing at a point farther removed from said forming handle.

5. The structure of claim 4 wherein each of said handles is biased against a stop, to normally occupy an open position.

6. The structure of claim 5 wherein biasing means for said clip forming handle is stronger than the biasing means for said clip feeding handle whereby upon actuation of said handles said feeding handle moves first to retract said feeding finger, and after said feeding finger is retracted said forming handle moves to clamp a clip which is in position between said forming portion of said magazine housing and said clip forming end of said clip forming handle.

7. The structure of claim 4, wherein means are provided to prevent actuation of the ligator when the said supply of clips is exhausted.

8. The structure of claim 1 wherein a clip is initially disposed in position between the forming portion of said magazine housing and the forming end of said forming handle when said handles are in their unactuated positions.

9. A surgical ligator to locate and clamp a substantially inverted U-shaped clip about a tubular member to close off the tubular member, said ligator comprising a magazine housing containing a supply of clips, a clip clamping handle and a clip feeding handle, pivotally secured to said ligator, said housing at its distal end and said distal end of said clip forming handle each terminating in a forming portion, said clip forming handle being operative to clamp one of said clips between said forming portions upon actuation of said handles, and feed means for sequentially feeding said clips between said forming portions to be clamped, said feed means including a feed element operatively connected to said clip feeding handle and shiftable upon actuation of said clip feeding handle to a ready postion adjacent the next clip to be fed from said magazine, and sequentially upon release of said clip feeding handle to a feed position in which said next clip is positioned by said feed element between said forming portions to be clamped.

10. A surgical ligator to locate and clamp a substantially inverted U-shaped clip about a tubular member to close off the tubular member, said ligator comprising a magazine housing containing a supply of said clips, said housing at its distal end terminating in a forming portion having a forming jaw a first handle having a cooperating forming jaw, a second clip feeding handle, and means operative to sequentially clamp one of said clips between said forming jaws as said handles are actuated, open said forming jaws upon initial release of said first handle, and feed the next said clip into said forming jaws upon release of said second handle.

* * * * *